US010544173B2

(12) United States Patent
McWilliams et al.

(10) Patent No.: US 10,544,173 B2
(45) Date of Patent: Jan. 28, 2020

(54) PHOSPHATE ESTER COMPOSITION AND USE

(71) Applicant: Sasol (USA) Corporation, Houston, TX (US)

(72) Inventors: Kurt McWilliams, Houston, TX (US); Willem Ghijsen, Houston, TX (US); Lynn Wells, Houston, TX (US)

(73) Assignee: Sasol (USA) Corporation, Houston, TX (US)

( * ) Notice: Subject to any disclaimer, the term of this patent is extended or adjusted under 35 U.S.C. 154(b) by 0 days.

(21) Appl. No.: 15/762,487

(22) PCT Filed: Oct. 6, 2016

(86) PCT No.: PCT/US2016/055657
§ 371 (c)(1),
(2) Date: Mar. 22, 2018

(87) PCT Pub. No.: WO2017/062557
PCT Pub. Date: Apr. 13, 2017

(65) Prior Publication Data
US 2018/0273556 A1    Sep. 27, 2018

Related U.S. Application Data

(60) Provisional application No. 62/239,319, filed on Oct. 9, 2015.

(51) Int. Cl.
*C07F 9/12* (2006.01)
*C08K 5/523* (2006.01)
*C10M 137/04* (2006.01)
*C09K 21/12* (2006.01)

(52) U.S. Cl.
CPC ............. *C07F 9/12* (2013.01); *C08K 5/523* (2013.01); *C09K 21/12* (2013.01); *C10M 137/04* (2013.01); *C10M 2223/041* (2013.01)

(58) Field of Classification Search
CPC ........... C10N 2240/08; C10N 2230/06; C10M 2223/04; C10M 2223/041
USPC ....................................................... 508/433
See application file for complete search history.

(56) References Cited

U.S. PATENT DOCUMENTS

| 3,816,311 A * | 6/1974 | Malec ............... C10M 3/00 508/267 |
| 6,204,227 B1 * | 3/2001 | Rao ............... C10M 137/04 508/433 |
| 2003/0078325 A1 | 4/2003 | Rose et al. |

FOREIGN PATENT DOCUMENTS

| JP | 8283473 | 10/1996 |
| WO | 2008030792 | 3/2008 |
| WO | 2010149690 | 12/2010 |
| WO | 2012067685 | 5/2012 |
| WO | 2013085724 | 6/2013 |

* cited by examiner

*Primary Examiner* — Vishal V Vasisth
(74) *Attorney, Agent, or Firm* — Bushman Werner, P.C.

(57) ABSTRACT

A phosphate ester composition comprising more than 50 mass % of a phosphate ester represented by Formula 1, wherein X, Y, and Z are independently selected from the group consisting of alkyl, heteroalkyl, heteroaryl or aryl, with at least one of X, Y and Z being aryl, represented by Formula 2, and wherein two or more of R3, R4 and R5 have from 1 to 10 carbon atoms, and the total number of carbon atoms in R3, R4 and R5 is from 3 to 30. The use of the phosphate ester composition as a flame retardant, a lubricant, an anti-wear additive, a hydraulic fluid, a self-extinguishing functional fluid, or an additive thereof.

Formula 1

$$X\text{-}O\text{-}\underset{\underset{Y}{|}}{\overset{\overset{O}{\|}}{P}}\text{-}O\text{-}Z$$
$$\phantom{X\text{-}O\text{-}}O$$

Formula 2

(structure of aryl group with substituents $R_2$, $R_3$, $R_4$, $R_5$, $R_6$ on benzene ring bonded through O)

14 Claims, No Drawings

PHOSPHATE ESTER COMPOSITION AND USE

CROSS REFERENCE TO RELATED APPLICATION

This application is a national phase application of PCT/US2016/055657 filed Oct. 6, 2016, which claims priority to U.S. Application No. 62/239,319 filed on Oct. 9, 2015, the disclosures of which are incorporated herein by reference for all purposes.

BACKGROUND OF THE INVENTION

THIS INVENTION relates to a phosphate ester composition and its use.

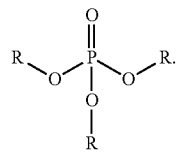

A

The use of phosphate esters of the above general formula (Formula A) as lubricants and flame retardants are well known in the art.

Tri-aryl Phosphate esters (see Formula B below) have been used for many years and are well known in the art as additives for flame retardant plasticizers, flame retardants, anti-wear agents, boundary lubricants, antioxidants as well as functional fluids (self-extinguishing hydraulic fluids).

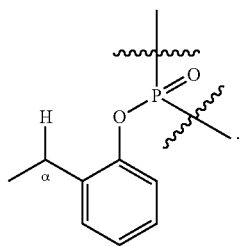

B

The first generation tri-aryl phosphates were based on phenol or refined cresols/xylenols from coal tar. These tri-aryl phosphate esters can be ortho [2, 6], meta [3, 5], or para [4] substituted (see Formula C below).

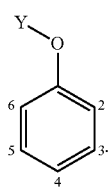

C

These "natural" materials have been slowly replaced with "synthetic" alkyl phenols (isopropyl, t-butyl, amyl, octyl, nonyl, etc.) as the performance (technical and regulatory) requirements have become more stringent. Unfortunately, in many applications the narrowing of technical performance requirements results in a trade-off with other attributes like regulatory performance and vice versa. Those versed in the art will recognize that for synthetic materials, alkyl substituent(s) is(are) most easily and directly connected at the 2, 4, and 6 positions of the phenol, as per Formula C. Commonly used synthetic alkyl phenols for phosphate esters are mostly substituted at the para (4) position. A drawback of para (mono) substituted synthetic aryl groups is that the resulting tris aryl phosphate ester is a high melt point solid or a high viscosity fluid. This has a deleterious effect on critical properties like liquidity, polymer miscibility, air entrainment, and pour point.

Combinations of triaryl, alkyl-diaryl, and di-alkyl-monoaryl phosphate esters have also been developed to meet specific requirements.

Performance requirements like volatility, exudation, toxicity (acute and neuro-) hydrolytic/oxidative/thermal stability and hazard classification are important properties of phosphate esters when used as flame retardants and lubricants. It is therefore a desire to improve the properties like volatility, exudation, neurotoxicity, without sacrificing pour point, viscosity or fluid life (hydrolytic, thermal, and oxidative stability).

US2003/0078325, incorporated herein by reference for all purposes, teaches the use of triaryl phosphate esters as flame retardants. The aryl ring has a single hydrocarbyl substituent on any carbon atom of the ring structure, with the total carbon number of the substituents being from 3 to 11. The phosphate esters are incorporated into polymer compositions alone or in combination with other flame retardants.

WO2010/149690, incorporated herein by reference for all purposes, discloses the use of triaryl phosphate esters as anti-wear agents with reduced neurotoxicity. Some or all of the aryl groups are mono-substituted with the same alkyl group, which may be located at the ortho-, meta-, or para-position of the ring structure.

SUMMARY OF THE INVENTION

The first aspect of the invention provides for a phosphate ester composition comprising more than 50 mass % of a phosphate ester represented by Formula 1 below,

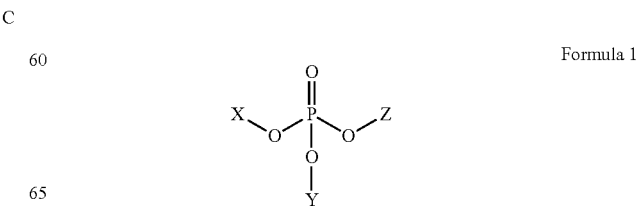

Formula 1 wherein X, Y, and Z are independently selected from the group consisting of alkyl, heteroalkyl, heteroaryl or aryl, with at least one of X, Y and Z being aryl, represented by Formula 2 below,

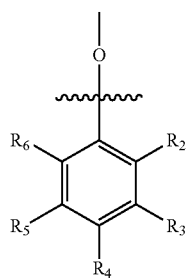

Formula 2 and wherein two or more of R3, R4 and R5 have from 1 to 10 carbon atoms, and the total number of carbon atoms in R3, R4 and R5 is from 3 to 30.

Preferably at least two or all of X, Y and Z are aryl, represented by Formula 2. The substituents R3, R4 and R5 of Formula 2 may be the same or different and may have different numbers of carbon atoms and structure. Substituents R3, R4 and R5 of Formula 2 may have from 1 to 6 or from 1 to 4 carbon atoms. The total number of carbon atoms in R3, R4 and R5 may be from 3 to 18, or from 3 to 12.

The Applicant has found that multiple short chain substituents on the aryl group leads to improved physical properties like melt point, viscosity and pour point of the phosphate esters.

Preferably the aryl group of Formula 2 is selected from the group consisting of 3-methyl-4-ethylphenol, 3-methyl-4-propylphenol, 3-methyl-4-isopropylphenol 3-methyl-4-butylphenol, 3-methyl-4-tert-butylphenol, 3-methyl-4-sec-butylphenol, 3-methyl-4-iso-butylphenol, 3-methyl-4-pentylphenol, 3-methyl-4-hexylphenol, 3-methyl-4-sec-hexylphenol, 3-methyl-4-heptylphenol, 3-methyl-4-octylphenol, 3-methyl-4-sec-octylphenol, 3-methyl-4-nonylphenol 3-methyl-4-decylphenol, 3-methyl-5-isopropylphenol, 3-isopropyl-4-methylphenol, 3,4,5-trimethylphenol, 3-ethyl-4-methylphenol, 3,5-dimethyl-4-ethylphenol, 3,5-dimethyl-4-propylphenol, 3,5-dimethyl-4-isopropylphenol, 3,5-dimethyl-4-butylphenol, 3,5-dimethyl-4-sec-butylphenol, 3,5-dimethyl-4-iso-butylphenol, 3,5-dimethyl-4-pentylphenol, 3,5-dimethyl-4-hexylphenol, 3,5-dimethyl-4-(1,1-dimethylpropyl)-phenol, 3,5-dimethyl-4-(1,1-dimethylbutyl)-phenol, 3,5-dimethyl-4-(1-ethyl,1-methylpropyl)-phenol, 3,5-dimethyl-4-heptylphenol, 3,5-dimethyl-4-octylphenol, 3,5-dimethyl-4-nonylphenol, 3,5-dimethyl-4-decylphenol, 3,4-diethylphenol, 3,5-diethylphenol, 3,4-dimethyl-5-ethylphenol, 4-methyl-3-isopropylphenol, 3-isopropyl-4-methylphenol, 3-methyl-4-(1,1-dimethylpropyl)-phenol, 3-methyl-4-(1,1-dimethylbutyl)-phenol, 3-methyl-4-(1-ethyl, 1-methylpropyl)-phenol.

More preferably the aryl group of Formula 2 is selected form the group consisting of 3,4,5-trimethylphenol, 3-methyl-4-ethylphenol, 3-methyl-4-isopropylphenol, 3-methyl-5-isopropylphenol, 3-methyl-4-tert-butylphenol, 3,5-dimethyl-4-ethyl phenol, 3,5-dimethyl-4-isopropylphenol, 3,5-dimethyl-4-propylphenol, 3,5-dimethyl-4-butylphenol 3,4-dimethyl-5-ethyl phenol, 4-methyl-3-isopropylphenol, 3-isopropyl-4-methylphenol, 3-methyl-4-(1,1-dimethylpropyl)-phenol, 3-methyl-4-(1,1-dimethylbutyl)-phenol, 3-methyl-4-(1-ethyl, 1-methylpropyl)-phenol.

Most preferably the aryl group of Formula 2 is selected from the group consisting of 3,4,5-trimethylphenol, 3-methyl-4-ethylphenol, 3-methyl-4-isopropylphenol, 3-methyl-5-isopropylphenol, 3-methyl-4-tert-butylphenol, 3,5-dimethyl-4-ethyl phenol, 3,5-dimethyl-5-isopropylphenol, 3,5-dimethyl-4-butylphenol.

When X, Y or Z is aryl, more than 90 mass %, more than 95 mass % or even more than 99 mass % of the phosphate esters in the composition has R2 and R6 being H (hydrogen) on all of the aryl groups present. The applicant has found that when R2 and R6 are hydrocarbyl groups with an active α-carbon hydrogen, this leads to an increase in toxicity of the phosphate ester.

The phosphate ester composition may comprise more than 60 mass %, or more than 70 mass %, or more than 80 mass % or even more than 90 mass % of the phosphate ester represented by Formula 1.

Preferably the phosphate ester of the present invention is according to Formula 3 below,

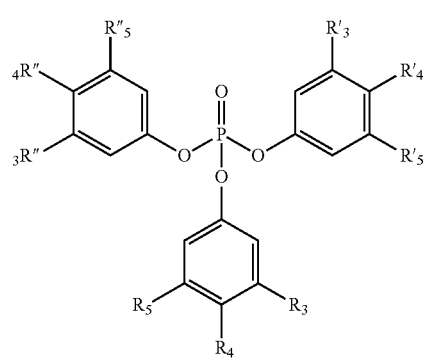

Formula 3 wherein R3, R4 and R5 are as described with respect to Formula 2. It will be understood that R'3, R'4, and R'5, as well as R"3, R"4, and R"5, are also as described with respect to R3, R4, and R5 in Formula 2. It will further be understood that each set of R3, R4, and R5; R'3, R'4, and R'5; and R"3, R"4, and R"5 may be the same as or differ from the other such sets in a particular phosphate ester.

According to a second aspect of the invention there is provided a phosphate ester composition as described herein, which comprises more than 50 mass % of a phosphate ester represented by Formula 4 below,

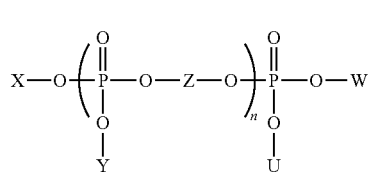

Formula 4 wherein Z is a hydrocarbyl or heterohydrocarbyl group having from 1 to 100 carbon atoms, X, Y, W and U are independently selected from the group consisting of alkyl, heteroalkyl, heteroaryl or aryl, with at least one of X, Y, U and W being aryl, represented by Formula 2 below, Formula 2

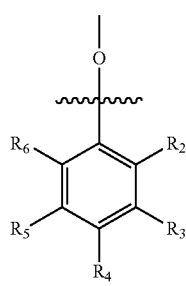

and wherein two or more of R3, R4 and R5 have from 1 to 10 carbon atoms, and the total number of carbon atoms in R3, R4 and R5 is from 3 to 30.

According to a third aspect of the invention, there is provided the use of the phosphate ester composition as described herein as a flame retardant, a lubricant, an anti-wear additive, a hydraulic fluid, a self-extinguishing functional fluid, or an additive therefore.

The applicant has found that multiple substituents located on the 3, 4, and/or 5 positions of the aryl group leads to improved physical properties like melt point, viscosity and pour point of phosphate (phosphite) esters, while avoiding neurotoxicity and GHS classification concerns.

As per the invention the following terms are defined as hereunder:

An "alkyl group" as defined herein and by IUPAC is a univalent groups derived from alkanes by removal of a hydrogen atom from any carbon atom —$C_nH_{2n+1}$.

A "heteroalkyl" as defined herein is an alkyl group in which at least one atom is an element other than carbon or hydrogen.

An "aryl group" as defined herein and by Hawley's Condensed Chemical Dictionary (13$^{th}$ Ed.) is a compound whose molecules have the ring structure characteristic of benzene, naphthalene, phenanthrene, anthracene, etc., (i.e., either the 6-carbon ring of benzene or the condensed 6-carbon rings of the other aromatic derivatives). For example, an aryl group may be phenyl $C_6H_5$ or naphthyl $C_{10}H_9$.

A "heteroaryl group" as defined herein is an aryl group in which one or more of the atoms in the ring is an element other than carbon, e.g. sulphur, nitrogen, etc.

A "hydrocarbyl group" as defined herein and by IUPAC is a univalent groups formed by removing a hydrogen atom from a hydrocarbon.

A "heterohydrocarbyl group" as defined herein is a univalent group formed by removing one hydrogen atom from a carbon atom of a heterohydrocarbon, that is a hydrocarbon compound which includes at least one hetero atom (that is, not being H or C), and which group bonds with one other moiety through the resultant free valency on that carbon atom.

DESCRIPTION OF EMBODIMENTS

The phosphate esters of the present invention are produced by methods which are well known in the art. Firstly, an alkylated phenol (cresol, xylenol, ethylphenol) is produced by alkylation of phenol (cresol, xylenol, ethylphenol) and/or by isomerisation of an alkylated phenol (cresol, xylenol, ethylphenol). U.S. Pat. No. 3,576,923, incorporated herein by reference for all purposes, discloses the alkylation of phenol with propylene to produce alkylated phenol. Those versed in the art will recognize that alkylating phenols can be accomplished via catalysed reaction of phenolic compounds with olefins and/or alcohols. The placement of substituents is directed by the orientation to the phenoxy group. Direct alkylation is limited to substituting the 2, 4, and/or 6 positions (Formula C) of the phenolic ring. It is commonly known that by adjusting the catalyst and conditions, the 2, 4, and/or 6 position can be favoured or disfavoured for alkyl substitution. Additionally the selection of olefin and/or alcohol reactant can have similar affect on the location (2, 4, and/or 6) of the alkyl substituent. Once prepared, the positional isomers (ortho, para) can be separated via distillation, crystallisation, and/or extraction.

Substituents at the meta (3, and/or 5) positions are not produced as a normal course of alkylation, but rather as the product of isomerisation. Isomerisation catalysts are known e.g. as disclosed in U.S. Pat. No. 3,936,410, incorporated herein by reference for all purposes, and some have the ability to both alkylate and isomerise. The alkylated phenol is then subjected to phosphorylation to yield the phosphate ester.

EXAMPLES

The Invention will now be described with reference to the following non limiting examples.

In the Examples:

GC means gas chromatography, Hewlett-Packer (HP) 7890 GC System with G4513A series injector (1.0 µL @ 250° C. (100:1 split), Open Lab control software, 50M×0.20 mm ID×0.50 µm HP-PONA (100% dimethylpolysiloxane), 1.0 L/min (constant flow mode) Helium, 40° C. (5 min hold) 10° C./min ramp rate to 310° C. (28 min hold), detection via flame ionization detector (FID) with air@ 450 mL/min, Hydrogen@ 35 mL/min, makeup Nitrogen@ 30 mL/min.

LCMS means liquid chromatography mass spectrometry, Thermo Ultimate-3000 Ultra High Performance Liquid Chromatography (UHPLC), Thermo Accucore RP-MS 50 mm (length)×2.1 mm (diameter)×2.6 micron column with water/acetonitrile as the mobile phase gradient programmed to 100% acetonitrile, flow rate of 0.3 cc/min, Advion CMS Expression single quadrapole, time of flight (tof), atmospheric pressure chemical ionization (APCI), positive ion (+) mode, mass scan range from 250-600 atomic mass units (amu).

HPLC means high performance liquid chromatography, Thermo U-3000 Ultra High Performance Liquid Chromatography (UHPLC), UV detection at 254 nm, 5 µL sample volume, ACE C18-PFP (ACE C18-PFP is a C18 bonded HPLC column with a pentafluorophenyl (PFP) phase), 150 mm (length)×4.6 mm (diameter)×3 micron, mobile phase 100% methanol at 0.2 ml/min, UV detection at 254 nm, 5 µL sample volume.

The melting point was measured via differential scanning calorimetry (DSC, TA instrument DSC Q20), standard cell, 10° C. ramp rate to 100° C., −1° C./min ramp rate to −90° C., 10° C./min ramp rate to 140° C.

The kinematic viscosity was measured using an Anton Paar SVM 3000 Viscometer following American Society for Testing and Materials (ASTM) test method D7042-"Standard Test Method for Dynamic Viscosity and Density of Liquids by Stabinger Viscometer (and the Calculation of Kinematic Viscosity)".

The pour point was measured via an iSL CPP 5Gs, following ASTM test method D97—"Standard Test Method for Pour Point of Petroleum Products".

Comparative Example 1—Synthesis of Tri-Cresyl Phosphate Ester (TCP)

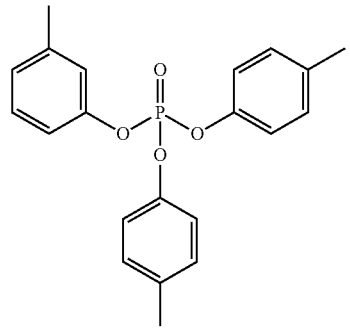

Mixed m-, p-Cresol (TCP)

A commercial sample of mixed m-,p-cresol (46% m-cresol, 53% p-cresol) was obtained and confirmed to be 99% m-,p-cresol (GC). This material was used as is without further purification. In a 1 litre reaction flask, 324 g of m-,p-cresol (MW-108, 3 moles), 93 ml of phosphorus oxychloride (MW-153.33, 1 mole), 3.838 g magnesium chloride and 6.1 g boiling chips were introduced. The reaction mixture was stirred and heated to 200° C. for over 4 hours. Once at this temperature the mixture was held at 200° C. for an additional 1 to 2 hours until there were no signs of ongoing reaction (i.e. no bubbling observed in the reaction flask). The reaction product was allowed to cool to at least 150° C. before proceeding to the purification step. The reaction product was purified by vacuum distillation. Fractions collected during the distillation were analysed by LCMS and HPLC to determine composition. Fractions of acceptable triaryl phosphate ester quality were recombined (290 g, 80% yield) and used for evaluation.

Comparative Example 2

Using a method similar to that outlined in Comparative Example 1 but with a different feedstock as shown in Table 1, the phosphate ester:(Tri-xylyl phosphate ester [TXP]) was synthesized.

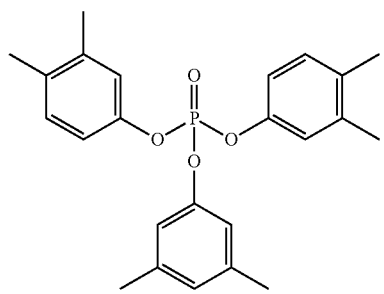

Mixed Xylyl (TXP)

Comparative Example 3

Using a method similar to that outlined in Comparative Example 1, but with a different feedstock as shown in Table 1, the phosphate ester (Tri-p-tert-butylphenol phosphate ester [TBPP]), was synthesized

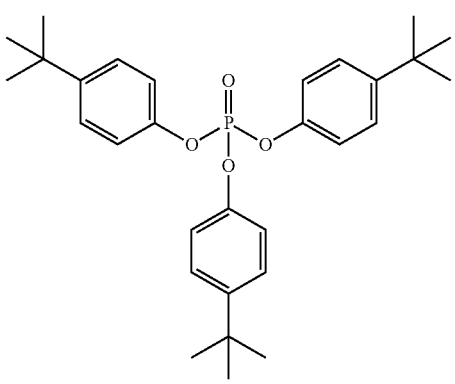

p-Tertbutyl phenyl (PTBP)

Example 1

Using a method similar to that outlined in Comparative Example 1, but with a different feedstock as shown in Table 1, the phosphate ester 4 (Tri-3-methyl-4-propylphenol phosphate ester was synthesized.

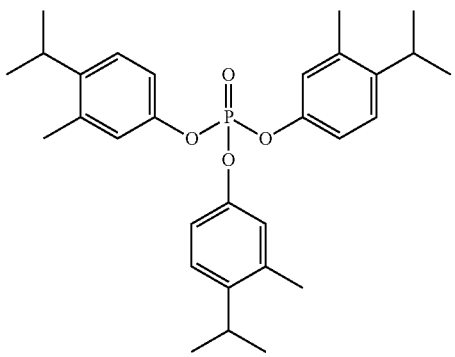 [SMILES: Cc1cc(OP(=O)(Oc2ccc(C(C)C)c(C)c2)Oc2ccc(C(C)C)c(C)c2)ccc1C(C)C]

The Properties of the phosphate esters made as per the Examples are summarised in Table 1.

TABLE 1

Phosphate Ester Examples

| | Comparative Example 1 TCP | Comparative Example 2 TXP | Comparative Example 3 TBPP | Example 1 Novel Phosphate Ester |
|---|---|---|---|---|
| R2 Substituent | None | None | None | None |
| R3 Substituent | Methyl (53%) | Methyl | None | Methyl |
| R4 Substituent | Methyl (47%) | Methyl | t-Butyl | i-Propyl |
| R5 Substituent | None | Methyl | None | None |
| R6 Substituent | None | None | None | None |
| Total number of carbon atoms in R3, R4 and R5 | 1 | 2 | 4 | 4 |
| Feedstock | m-,p-cresol | Xylenols | p-tert-butyl phenol | 3-methyl-4-isopropyl phenol |
| Phenol Co-feed, % | 0 | 0 | 0 | 0 |
| Purity, % | | | >98 | >98 |
| Yield, % | | | | |
| Form @ Ambient Temperature, ≈25 C. | Liquid | Liquid | Solid | Liquid |
| Melt Point[1], C. | — | — | 104 | — |
| Kinematic Viscosity[2] @ 40 C., cSt | 22 | 42 | — | 332 |
| Kinematic Viscosity[2] @ 100 C., cSt | 4 | 5 | — | 13 |
| Pour Point[3], C. | −33 | −25 | — | −7 |

[1]melting point measured via differential scanning calorimetry (DSC, TA Instruments DSC Q20)
[2]kinematic viscosity measured using an Anton Paar SVM 3000 Viscometer
[3]pour point measured via an iSL CPP 5Gs, following ASTM D97

The applicant has found (Example 1) that by eliminating substituents at the 2, and/or 6 position that regulatory neurotoxicity concerns are addressed, and that by varying the i) number (at least two), ii) location (3, 4, and/or 5) and iii) size of substituents that improvements in physical properties (like viscosity and pour point, Table 1) can be realized versus mono-substituted aryl phosphate esters. Otherwise solid 4-monoalkyl aryl(phenyl) phosphate esters can be redesigned into room temperature liquids of less than 0° C. pour point while maintaining equivalent molecular weight.

Furthermore, the improvement in certain physical properties does not come at the expense of properties like volatility, boiling point, or acute toxicity (GHS Classification). Additionally, the improved viscosity reduces the need to add phenyl groups, which are prone to hydrolysis and have acute toxicity (marine pollutant) issues.

The effect of multiply substituted 3, 4, and/or 5 aryl groups on the finished phosphate ester is not discernible from the physical characteristics of the starting materials, (see Table 2).

TABLE 2

Physical Properties of Alkyl Phenols.

| | Alkyl Phenol | M.W. | Melt Point, ° C. | Boiling Point, ° C. |
|---|---|---|---|---|
| C4 | 4-Tert-Butyl Phenol | 150 | 98 | 237 |
| | 4-Isopropyl-3-MethylPhenol | 150 | 110 | 238 |

Although specific embodiments of the invention have been described herein in some detail, this has been done solely for the purposes of explaining the various aspects of the invention, and is not intended to limit the scope of the invention as defined in the claims which follow. Those skilled in the art will understand that the embodiment shown and described is exemplary, and various other substitutions, alterations and modifications, including but not limited to those design alternatives specifically discussed herein, may be made in the practice of the invention without departing from its scope.

We claim:

1. A phosphate ester composition comprising more than 50 mass % of a phosphate ester represented by Formula 1,

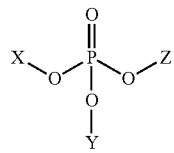

Formula 1 wherein X, Y, and Z are independently selected from the group consisting of alkyl, heteroalkyl, heteroaryl or aryl, with at least one of X, Y and Z being aryl, represented by Formula 2,

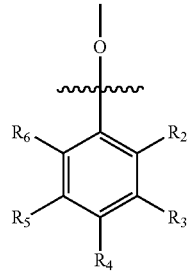

Formula 2 and wherein two or more of $R_3$, $R_4$ and $R_5$ are substituents having from 1 to 10 carbon atoms, and the total number of carbon atoms in $R_3$, $R_4$ and $R_5$ is from 3 to 30, wherein the substituents $R_3$, $R_4$, and $R_5$ of Formula 2 are different, wherein $R_2$ and $R_6$ are hydrogen, and wherein in the case of two of $R_3$, $R_4$ and $R_5$ being substituents, the remaining $R_3$, $R_4$, or $R_5$ is hydrogen.

2. The phosphate ester of claim 1, wherein at least two of X, Y and Z are aryl, represented by formula 2.

3. The phosphate ester of claim 1, wherein R3, R4 and R5 of Formula 2 have from 1 to 6 carbon atoms.

4. The phosphate ester of claim 1, wherein R3, R4 and R5 of Formula 2 have from 1 to 4 carbon atoms.

5. The phosphate ester of claim 1 wherein the total number of carbon atoms in R3, R4 and R5 is from 3 to 18.

6. The phosphate ester composition of claim 1 wherein the total number of carbon atoms in R3, R4 and R5 is from 3 to 12.

7. The phosphate ester of claim 1 wherein the aryl group of Formula 2 is selected from the group consisting of 3-methyl-4-ethylphenol, 3-methyl-4-propylphenol, 3-methyl-4-isopropylphenol 3-methyl-4-butylphenol, 3-methyl-4-tert-butylphenol, 3-methyl-4-sec-butylphenol, 3-methyl-4-iso-butylphenol, 3-methyl-4-pentylphenol, 3-methyl-4-hexylphenol, 3-methyl-4-sec-hexylphenol, 3-methyl-4-heptylphenol, 3-methyl-4-octylphenol, 3-methyl-4-sec-octylphenol, 3-methyl-4-nonylphenol 3-methyl-4-decylphenol, 3-methyl-5-isopropylphenol, 3-isopropyl-4-methylphenol, 3-ethyl-4-methylphenol, 3,5-dimethyl-4-ethylphenol, 3,5-dimethyl-4-propylphenol, 3,5-dimethyl-4-isopropylphenol, 3,5-dimethyl-4-butylphenol, 3,5-dimethyl-4-sec-butylphenol, 3,5-dimethyl-4-iso-butylphenol, 3,5-dimethyl-4-pentylphenol, 3,5-dimethyl-4-hexylphenol, 3,5-dimethyl-4-(1,1-dimethylpropyl)-phenol, 3,5-dimethyl-4-(1,1-dimethylbutyl)-phenol, 3,5-dimethyl-4-(1-ethyl, 1-methylpropyl)-phenol, 3,5-dimethyl-4-heptylphenol, 3,5-dimethyl-4-octylphenol, 3,5-dimethyl-4-nonylphenol, 3,5-dimethyl-4-decylphenol, 3,4-dimethyl-5-ethylphenol, 4-methyl-3-isopropylphenol, 3-isopropyl-4-methylphenol, 3-methyl-4-(1,1-dimethylpropyl)-phenol, 3-methyl-4-(1,1-dimethylbutyl)-phenol, 3-methyl-4-(1-ethyl,1-methylpropyl)-phenol.

8. The phosphate ester of claim 1 wherein the phosphate ester is represented by Formula 3:

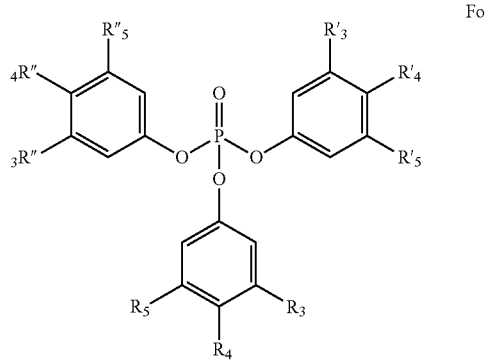

Formula 3 wherein two or more of $R_3$, $R_4$ and $R_5$ are substituents having from 1 to 10 carbon atoms, and the total number of carbon atoms in $R_3$, $R_4$ and $R_5$ is from 3 to 30, and wherein the substituents $R_3$, $R_4$, and $R_5$ are different, and wherein in the case of two of $R_3$, $R_4$, and $R_5$ being said substituents, the remaining $R_3$, $R_4$, or $R_5$ is hydrogen, two or more of $R'_3$, $R'_4$ and $R'_5$ are substituents having from 1 to 10 carbon atoms, and the total number of carbon atoms in $R'_3$, $R'_4$ and $R'_5$ is from 3 to 30, and wherein the substituents $R'_3$, $R'_4$, and $R'_5$ are different, and wherein in the case of two of $R'_3$, $R'_4$, and $R'_5$ being substituents, the remaining $R'_3$, $R'_4$, or $R'_5$ is hydrogen, two or more of $R''_3$, $R''_4$ and $R''_5$ are substituents having from 1 to 10 carbon atoms, and the total number of carbon atoms in $R''_3$, $R''_4$ and $R''_5$ is from 3 to 30, and wherein the substituents $R''_3$, $R''_4$, and $R''_5$ are different, and wherein in the case of two of $R''_3$, $R''_4$, and $R''_5$ being substituents, the remaining $R''_3$, $R''_4$, or $R''_5$ is hydrogen.

9. A phosphate ester composition comprising more than 50 mass % of a phosphate ester represented by Formula 4,

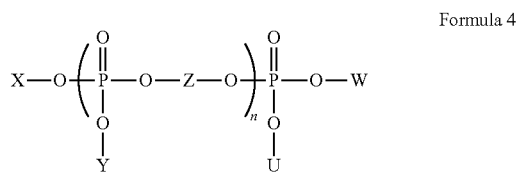

Formula 4 wherein Z is a hydrocarbyl or heterohydrocarbyl group having from 1 to 100 carbon atoms, n is 1, and X, Y, W and U are independently selected from the group consisting of alkyl, heteroalkyl, heteroaryl or aryl, with at least one of X, Y, U and W being aryl, represented by Formula 2,

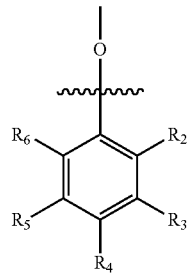

Formula 2 and wherein two or more of $R_3$, $R_4$ and $R_5$ are substituents having from 1 to 10 carbon atoms, and the total number of carbon atoms in $R_3$, $R_4$ and $R_5$ is from 3 to 30, and wherein the substituents $R_3$, $R_4$, and $R_5$ are different, wherein $R_2$ and $R_6$ are hydrogen, and wherein in the case of two of $R_3$, $R_4$, and $R_5$ being substituents, the remaining $R_3$, $R_4$, or $R_5$ is hydrogen.

10. The phosphate ester of claim 9 wherein the substituents R3, R4 and R5 of Formula 2 have from 1 to 6 carbon atoms.

11. The phosphate ester of claim 9 wherein the substituents R3, R4 and R5 of Formula 2 have from 1 to 4 carbon atoms.

12. The phosphate ester of claim 9 wherein the total number of carbon atoms in R3, R4 and R5 is from 3 to 18.

13. The phosphate ester of claim 9 wherein the total number of carbon atoms in R3, R4 and R5 is from 3 to 12.

14. The phosphate ester of claim 9 wherein the aryl group of Formula 2 is selected from the group consisting of 3-methyl-4-ethylphenol, 3-methyl-4-propylphenol, 3-methyl-4-isopropylphenol 3-methyl-4-butylphenol, 3-methyl-4-tert-butylphenol, 3-methyl-4-sec-butylphenol, 3-methyl-4-iso-butylphenol, 3-methyl-4-pentylphenol, 3-methyl-4-hexylphenol, 3-methyl-4-sec-hexylphenol, 3-methyl-4-heptylphenol, 3-methyl-4-octylphenol, 3-methyl-4-sec-octylphenol, 3-methyl-4-nonylphenol 3-methyl-4-decylphenol, 3-methyl-5-isopropylphenol, 3-isopropyl-4-methylphenol, 3-ethyl-4-methylphenol, 3,5-dimethyl-4-ethylphenol, 3,5-dimethyl-4-propylphenol, 3,5-dimethyl-4-isopropylphenol, 3,5-dimethyl-4-butylphenol, 3,5-dimethyl-4-sec-butylphenol, 3,5-dimethyl-4-iso-butylphenol, 3,5-dimethyl-4-pentylphenol, 3,5-dimethyl-4-hexylphenol, 3,5-dimethyl-4-(1,1-dimethylpropyl)-phenol, 3,5-dimethyl-4-(1,1-dimethylbutyl)-phenol, 3,5-dimethyl-4-(1-ethyl,1-methylpropyl)-phenol, 3,5-dimethyl-4-heptylphenol, 3,5-dimethyl-4-octylphenol, 3,5-dimethyl-4-nonylphenol, 3,5-dimethyl-4-decylphenol, 3,4-dimethyl-5-ethylphenol, 4-methyl-3-isopropylphenol, 3-isopropyl-4-methylphenol, 3-methyl-4-(1,1-dimethylpropyl)-phenol, 3-methyl-4-(1,1-dimethylbutyl)-phenol, 3-methyl-4-(1-ethyl,1-methylpropyl)-phenol.

\* \* \* \* \*